United States Patent
DeSalvo et al.

(10) Patent No.: US 7,522,702 B2
(45) Date of Patent: *Apr. 21, 2009

(54) SOFT X-RAY RADIATION FOR BIOLOGICAL PATHOGEN DECONTAMINATION AND MEDICAL STERILIZATION APPLICATIONS

(75) Inventors: John Richard DeSalvo, Satellite Beach, FL (US); Charles M. Newton, Palm Bay, FL (US); Carol Ann Gamlen, Melbourne, FL (US); William Thomas Silfvast, Saint Helena, CA (US); Gregory Michael Shimkaveg, Oviedo, FL (US)

(73) Assignee: Harris Corporation, Melbourne, FL (US)

( * ) Notice: Subject to any disclaimer, the term of this patent is extended or adjusted under 35 U.S.C. 154(b) by 56 days.

This patent is subject to a terminal disclaimer.

(21) Appl. No.: 11/511,671

(22) Filed: Aug. 29, 2006

(65) Prior Publication Data

US 2008/0056448 A1  Mar. 6, 2008

(51) Int. Cl.
*G21K 5/00* (2006.01)
(52) U.S. Cl. ........................... 378/64; 378/122
(58) Field of Classification Search .............. 378/64, 378/101–112, 114–116, 122; 250/455.11
See application file for complete search history.

(56) References Cited

U.S. PATENT DOCUMENTS

| | | | |
|---|---|---|---|
| 2,922,060 A | 1/1960 | Rajewsky | |
| 7,217,235 B2 * | 5/2007 | Kindlein et al. | 600/1 |
| 7,280,636 B2 * | 10/2007 | Morrison et al. | 378/122 |
| 2004/0101958 A1 | 5/2004 | Shimp | |
| 2007/0189459 A1 | 8/2007 | Eaton et al. | |
| 2007/0237296 A1 * | 10/2007 | Wyatt et al. | 378/64 |
| 2008/0181364 A1 * | 7/2008 | DeSalvo et al. | 378/138 |

FOREIGN PATENT DOCUMENTS

| | | |
|---|---|---|
| AU | 437727 | 7/1973 |
| EP | 1 227 126 | 7/2002 |
| GB | 1 602 253 | 11/1981 |
| WO | 02/053195 | 7/2002 |
| WO | 02/075771 | 9/2002 |
| WO | 03/086479 | 10/2003 |

* cited by examiner

*Primary Examiner*—Jurie Yun
(74) *Attorney, Agent, or Firm*—Harness, Dickey & Pierce, P.L.C.

(57) ABSTRACT

A method is provided for decontaminating biological pathogens in a contaminated environment. The method includes: tailoring x-ray radiation to match the absorption characteristics of a contaminated environment; generating x-ray radiation having a diffused radiation angle in accordance with the absorption characteristics of the contaminated environment; and directing the x-ray radiation towards the contaminated environment.

11 Claims, 4 Drawing Sheets

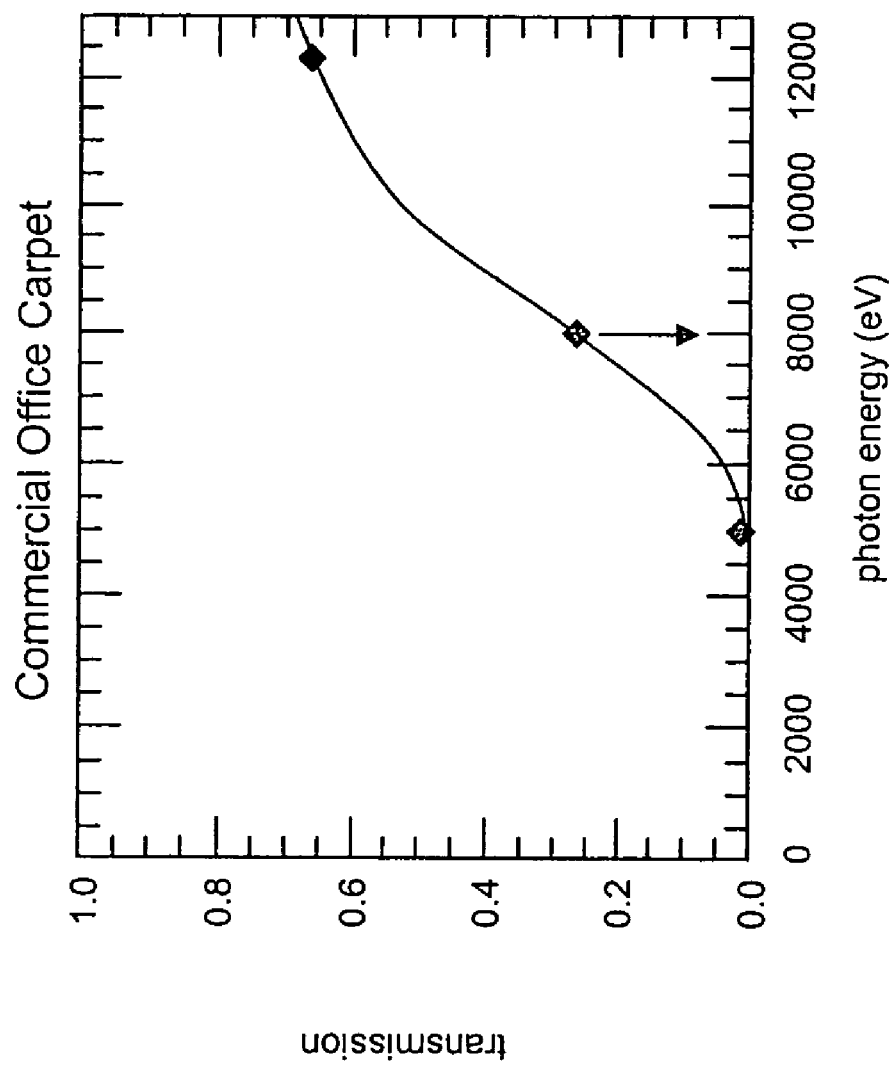

SOFT X-RAY RADIATION FOR BIOLOGICAL PATHOGEN DECONTAMINATION AND MEDICAL STERILIZATION APPLICATIONS

FIELD

The present disclosure relates generally to decontamination of biological hazards and, more particularly, to a rapid and non-destructive decontamination technique which employs soft x-ray radiation to eradicate biological hazards.

BACKGROUND

An Associated Press article in March 2005, reported at a meeting hosted by the Global Police Agency, Interpol sounded an urgent warning that bioterrorism is the world's greatest security threat and police are ill-equipped to handle an attack. In his opening remarks, Interpol Secretary General Ronald K. Noble stated "There is no criminal threat with greater potential danger to all countries, regions and people in the world than the threat of bioterrorism." In the United States, domestic bioterrorism attacks in the fall of 2001 demonstrated a costly vulnerability of society. The most significant release of anthrax spores in 2001 (in terms of number of spores released) was in the office suite of the U.S. Senate Majority Leader on the fifth floor of the Hart Senate Office Building. This event resulted in the closure of the entire building from Oct. 17, 2001 until Jan. 22, 2002. Three separate applications of chlorine dioxide gas were attempted to decontaminate the office suite and the HVAC system in the southeast quadrant of the building. The rest of the building was disinfected with chlorinated liquids and antimicrobial foam.

The Trenton, N.J. Postal Center which handled the contaminated letters was closed for three and a half years, finally reopening in March 2005. In a far less substantial release at NBC News in New York, one-half of a floor had to be evacuated for one month, and all the carpet from that area was ripped out and disposed of. Such response, while necessary for safety, caused a great deal of disruption for the people involved and cost millions of dollars. The scope of bioterrorism attacks, affecting both private sector and government facilities, indicates a vulnerability that is widespread.

Therefore, it is desirable to develop a rapid and non-destructive decontamination and sterilization technique for biological hazards. The statements in this section merely provide background information related to the present disclosure and may not constitute prior art.

SUMMARY

A method is provided for decontaminating biological pathogens in a contaminated environment. The method includes: tailoring the x-ray spectrum to match the absorption characteristics of the contaminated environment; determining a dose of x-ray radiation needed to kill a biological pathogen residing in the contaminated environment; generating x-ray radiation having a diffused range of source angles; and directing a calibrated dose of the diffused x-ray radiation towards the contaminated environment.

In one aspect of this disclosure, the x-ray source has been specifically designed to generate diffuse radiation. For example, the anode may employ a concave shaped emitting surface that spatially disperses the electron current density which generates the emitted x-radiation. In another example, a secondary electrode may be disposed within the vacuum housing near the filament for shaping the electric field to disperse the electrons.

Further areas of applicability will become apparent from the description provided herein. It should be understood that the description and specific examples are intended for purposes of illustration only and are not intended to limit the scope of the present disclosure.

DRAWINGS

FIG. 5 is a graph illustrating how x-ray radiation having different photon energy levels penetrates commercial grade office carpet.

The drawings described herein are for illustration purposes only and are not intended to limit the scope of the present disclosure in any way.

DETAILED DESCRIPTION

Electromagnetic radiation offers many advantages over chemicals or heat as a decontaminant. Radiation is generally much less disturbing to the object being sterilized than either reactive oxidizers like chlorine or high temperatures. In addition, radiation can be applied with less labor and hence involve less risk. Unfortunately, germicidal ultraviolet radiation will not penetrate many common materials such as paper, plastics, fibers or metals. In contrast, high energy gamma rays will penetrate many objects, but require very large doses due to the small probability of interaction with the biological pathogens of interest, thereby further requiring massive shielding for safe use. X-ray radiation has been found to be a suitable decontaminant, is penetrating, and can be controlled simply and safely.

Figure 1:
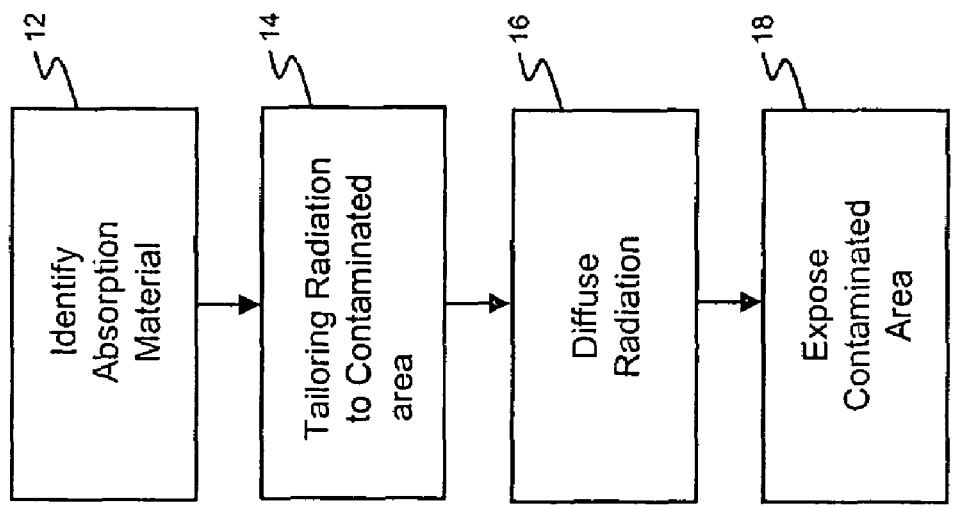
FIG. 1 is a flowchart illustrating an exemplary decontamination technique which employs x-ray radiation.
Figure 2:
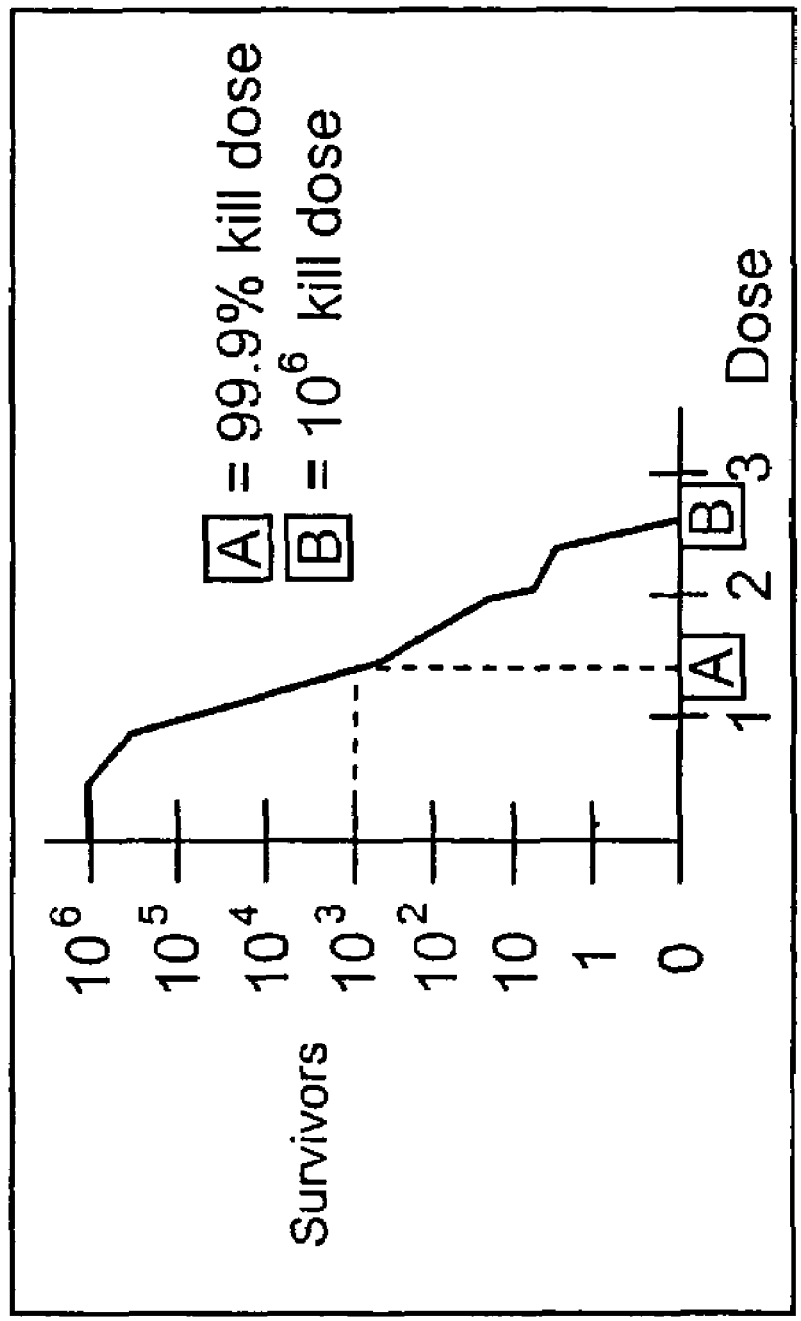
FIG. 2 is a graph illustrating a kill curve for an exemplary biological pathogen.

FIG. 1 illustrates a rapid and non-destructive decontamination technique using x-ray radiation. When confronted with a contaminated environment, the primary absorption materials found in the environment are first identified at 12. Henceforth in this application we define the term "contaminated environment" as the object surrounding the pathogen. Such environments include absorption materials, for example, porous materials, organic materials, or complex assemblies such as microelectronics, for which the common methods of sterilization would be ineffective or destructive.

Next, the x-ray spectrum is tailored at 14 to match the absorption characteristics of the contaminated environment. In particular, the photon energy for the x-radiation is selected based on the x-ray transmission of the absorption materials identified in the contaminated environment. In addition, the dose of radiation needed to kill a biological hazard found in the environment is determined. For instance, the amount of electrical power and the duration of the radiation for a given area are computed as further described below. X-ray radiation is then applied to the contaminated environment. More specifically, the x-ray radiation having a diffused radiation angle is generated 16 and then directed towards 18 the contaminated area.

The practicality of this concept was demonstrated with a feasibility experiment. Samples of $10^6$ spores of *Bacillus subtilis*, which is a non-hazardous surrogate for *Bacillus anthracis*, were first placed in a test environment and exposed to a dose of x-ray radiation from a copper anode source having photon energies primarily around 8 keV. Irradiated and control samples were then individually incubated in soy broth at 35° C. for a week. Samples with one or more viable spores produce a cloudy infusion, while a completely sterilized sample remains clear. Our results showed that at delivered doses of over 4.5 J/cm², all samples were completely sterilized. The highest dose delivered to a sample that remained incompletely sterilized was 330 mJ/cm². Hence the 8 keV x-ray kill dose for $10^6$ spores of our surrogate fell somewhere between those two values.

Design of the x-ray source for decontamination applications is qualitatively different than for conventional x-ray tubes used for imaging. Importantly, the x-ray emitting area needs to be large so that sharp shadows in the illuminated volume are avoided. If sharp, high contrast shadows occur, microscopic pathogens could escape from the irradiation and circumvent the desired sterilization. Since x-rays are emitted from the outermost few microns of anode material which receives electron bombardment, the electron beam must be tailored to impinge over the full surface of the anode to achieve the largest effective source size. To this end, the electric field guiding the electrons must be crafted to diverge from the cathode and intersect the anode uniformly, to the greatest extent possible. This technique of tailoring the electric field distribution in the x-ray source is referred to herein as "field sculpting".

Figure 3:
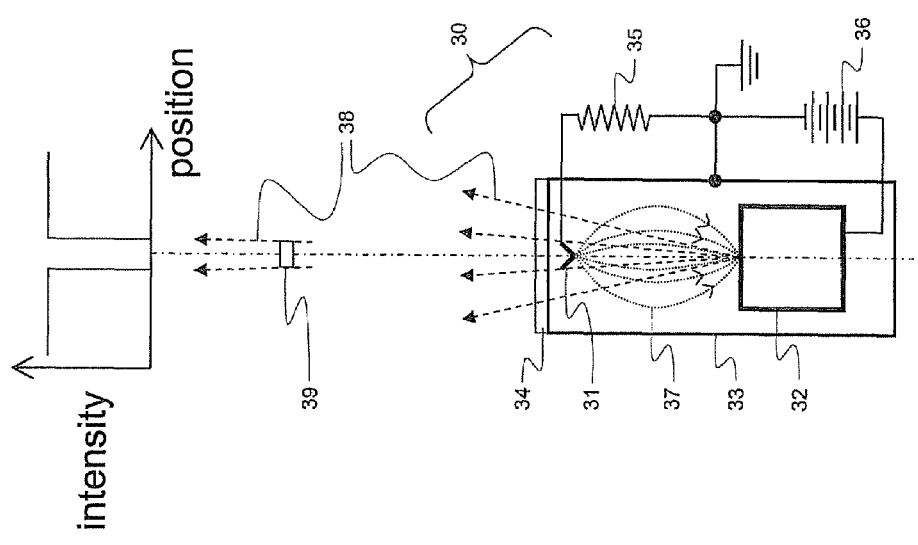
FIG. 3 is a diagram depicting a conventional x-ray source.

Traditional x-ray sources used for imaging applications are designed as point-source emitters as shown in FIG. 3. Briefly, the x-ray source 30 is comprised of a cathode 31 and an anode 32 housed in an electrically conducting, grounded vacuum enclosure 33. The cathode 31 is electrically coupled via a load resistor 35 to a power supply 36. In operation, the cathode emits electrons when energized by the power supply 36. Emitted electrons (paths indicated by dotted lines 37) follow the electric fields and are accelerated towards the anode 32 which in turn emits x-ray radiation 38 (indicated by dashed lines) when the electrons impinge upon its surface. The cathode acquires a voltage (called the self-bias voltage) equal to the product of the load resistance and the emitted electron current. The combination of the cathode's acquired negative voltage, the enclosure ground, and the anode's positive high voltage forms a three-element electron lens, which focuses the electron current density to a small point. All x-ray radiation is generated at that point. Although desirable in imaging applications, this source configuration produces sharp shadows of absorbing materials 39 (which in application would be objects in the contaminated environment such as carpet fibers or electronic leads, for example) as indicated by the plot of intensity versus position behind the absorber. This may obscure the biological hazards and dramatically reduce decontamination efficacy.

Figure 4:
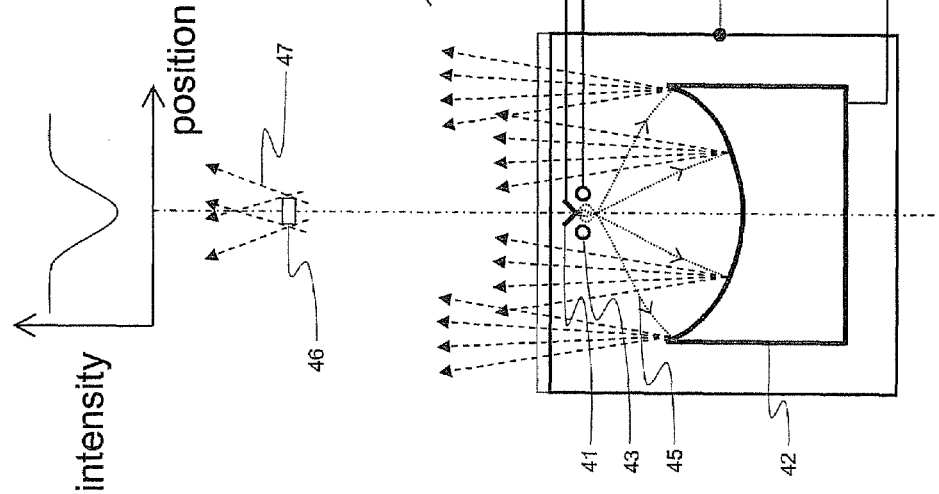
FIG. 4 is a diagram depicting an x-ray source that has been modified to diffuse the radiation.

To make a diffuse x-ray lamp, it is necessary for a large area of the anode surface to emit x-rays. This requires the electron current to be spread wide, avoiding focusing effects. A modified x-ray source design is shown in FIG. 4. Three major modifications have been made to the classical design to accomplish this electron spreading. First, the cathode 41 is electrically tied to ground to avoid any self-bias voltage; the load resistor has been removed. Second, the surface figure of the anode 42 has been curved into a concave shape. Third, a supplementary electrode called the field sculpting electrode 43 is placed surrounding the electron current in the close vicinity to the cathode and is biased by a variable voltage 44. Although any one of these changes produces a partial result, the combination of these three changes causes the electric field lines to spread out, drawing the electron current 45 to impact uniformly across the anode surface. In turn, this results in an illumination of the absorber 46 which is diffuse, as indicated by the x-ray trajectories 47. The term "diffused radiation angle" refers to the source possessing the characteristic of a large radiating surface area as viewed by the absorbing material in the contaminated environment, resulting in lowered shadow contrast to avoid having local unirradiated regions. The resulting x-ray intensity pattern behind the absorber does not fall to zero, meaning even if pathogens were to reside behind the absorber they would still be irradiated.

Additionally, this x-ray source may be configured to irradiate over a very wide angle by positioning the output window as close as possible to the anode. X-rays are generated in the first few micrometers of the anode surface that is bombarded with electron current. Any location in the irradiated zone in a clear line of sight to the active anode surface will receive x-rays. The design and location of the output window can be configured to transmit close to a full $2\pi$ steradians of irradiated solid angle.

Furthermore, the radiation should thoroughly penetrate the materials covering, surrounding or otherwise obstructing the biological hazard. The x-ray radiation should not pass through the contaminated materials having failed to interact with the biological hazard. High energy x-ray photons will penetrate denser materials, but the resultant scattering cross-section of the photon is reduced. Therefore, a larger flux of x-ray photons is required, leading to longer exposure times to achieve a sufficient kill dose. This is the reason it is advantageous to choose the x-ray photon energy consistent with the materials needing to be decontaminated X-ray radiation of different photon energies penetrates a contaminated environment to different depths. The x-ray transmission, T, of the absorption material in the contaminated environment is given by $$T=e^{-\sigma nL},$$

Where σ is the absorption material's atomic cross section, n is the number density (atoms per cubic centimeter), and L is the path length that the x-rays follow through the absorption material. The material's atomic cross section is a function of the photon energy. Above the K-shell binding energy, the cross section varies as the inverse square of the photon energy. This strong relationship results in a wide range of transmission T versus energy. We choose to use an energy at which $T=e^{-1}$. FIG. 5 illustrates an example of this effect, wherein the contaminated environment is carpet. At 5 keV, only 1% of the radiation penetrates to the bottom of the carpet sample so that deeply embedded bacteria may survive. At 12 keV, most radiation goes through the carpet without interacting with the bacteria. However, at 8 keV, the radiation effectively penetrates the carpet to kill any embedded bacteria. Therefore, x-ray radiation having a photon energy of 8 keV is preferable for decontaminating a biological pathogen found in a carpet or other porous material. A photon energy level of 8 keV may be achieved with an x-ray source configured in a manner described above with a cathode comprised of tungsten and an anode comprised of copper. In contrast, radiation having a photon energy of 18 keV is needed to sufficiently penetrate pine wood (approximately 1.5" thick). Thus, the photon energy for the radiation should be selected based on the absorption materials found in the contaminated environment. Although the cathode was comprised of tungsten in this example, it is readily understood that x-ray source may employs different types of cathodes, including but not limited to thermionic emitters, such as tungsten-thorium alloy, tantalum, and others, as well as cold cathodes which could be metallic wires or exotic materials like carbon nanotubes.

The photon energies produced by an x-ray source can be scaled through the judicious choice of the anode materials. This is understood through Moseley's empirical formula for k-alpha x-rays. The formula shows the x-ray photon energy is dependent on the square of the atomic number of an element $$E_K \alpha (Z-1)^2$$

Where $E_K$ is the x-ray photon energy and Z is the atomic number of the anode material. For instance, an x-ray source having a molybdenum (Z=42) anode will generate radiation having a photon energy of 18 keV. In comparison, a silver (Z=47) anode can generate radiation having a photon energy of 22 keV. It is envisioned that x-ray sources will be fabricated with different anode materials to ensure penetration through various material compositions providing decontamination radiation inside an object in addition to surface decontamination.

The above description is merely exemplary in nature and is not intended to limit the present disclosure, application, or uses. The decontamination and sterilization technique described above can be transitioned to a number of different applications, including but not limited to portable biological pathogen decontamination for civilian and military uses, remotely-deployable payload for delivery by unmanned platforms, mail sorting sterilization, baggage sterilization, battlefield medical sterilizer and mold spore eradication.

What is claimed is:

1. A method for decontaminating biological pathogens in a contaminated environment, comprising:
   tailoring x-ray radiation spectrum to match absorption characteristics of a contaminated environment;
   generating x-ray radiation having a diffused radiation angle by accelerating electrons from a cathode towards a concave surface of an anode and in accordance with the absorption characteristics of the contaminated environment; and
   directing the x-ray radiation towards the contaminated environment.

2. The method of claim 1 wherein tailoring x-ray radiation further comprises determining a photon energy for the x-ray radiation that adequately penetrates the absorption materials found in the contaminated environment.

3. The method of claim 1 wherein tailoring x-ray radiation further comprises determining a dose of x-ray radiation needed to kill a biological pathogen residing in the contaminated environment.

4. The method of claim 1 further comprising generating x-ray radiation having the diffused radiation angle by electrically grounding the cathode to eliminate any self-bias voltage.

5. The method of claim 1 further comprising generating x-ray radiation having the diffused radiation angle by disposing a secondary electrode proximate to the cathode for shaping the x-ray radiation.

6. A method for decontaminating biological pathogens in a contaminated environment, comprising:
   identifying a primary absorption material found in the contaminated environment;
   determining a dose of x-ray radiation needed to kill a biological pathogen residing in the contaminated environment, the x-ray radiation having a photon energy that penetrates the absorption material;
   generating x-ray radiation having a diffused radiation angle; and
   directing the diffused x-ray radiation towards the contaminated environment.

7. The method of claim 6 wherein determining a dose of x-ray radiation further comprises
   placing a known biological pathogen in a test environment;
   exposing the test environment to a calibrated dose of x-ray radiation; and
   measuring a survival rate of the biological pathogens in the test environment prior to decontaminating the contaminated environment.

8. The method of claim 7 further comprising placing an absorption material of interest between the source of x-ray radiation and the known biological pathogen.

9. The method of claim 6 further comprising generating the x-ray radiation having a photon energy approximately 8 keV when the absorption material in the contaminated environment is carpet.

10. The method of claim 6 further comprising generating the x-ray radiation having a photon energy approximately 18 keV when the absorption material in the contaminated environment is wood.

11. A method for decontaminating biological pathogens in a contaminated environment, comprising:
    identifying a primary absorption material found in the contaminated environment;
    determining a dose of x-ray radiation needed to kill a biological pathogen residing in the contaminated environment, the x-ray radiation having a photon energy that penetrates the absorption material;
    generating x-ray radiation having a diffused radiation angle by accelerating electrons from a cathode towards a concave surface of an anode, electrically grounding the cathode to eliminate self-bias voltage, and disposing a secondary electrode proximate to the cathode for shaping the radiation; and
    directing the diffused x-ray radiation towards the contaminated environment.

* * * * *